United States Patent
Keren et al.

(10) Patent No.: US 6,749,598 B1
(45) Date of Patent: Jun. 15, 2004

(54) APPARATUS AND METHODS FOR TREATING CONGESTIVE HEART DISEASE

(75) Inventors: Gadi Keren, Kiryiat Ono (IL); Ascher Shmulewitz, Mercer Island, WA (US)

(73) Assignee: Flowmedica, Inc., Freemont, CA (US)

( * ) Notice: Subject to any disclaimer, the term of this patent is extended or adjusted under 35 U.S.C. 154(b) by 0 days.

(21) Appl. No.: 09/229,390

(22) Filed: Jan. 11, 1999

(51) Int. Cl.⁷ .............................................. A61M 31/00
(52) U.S. Cl. ........................ 604/508; 604/509; 604/8; 604/9; 604/915
(58) Field of Search .................... 604/284, 8, 9, 604/523, 529, 912, 919, 915, 96, 500, 507, 508, 509

(56) References Cited

U.S. PATENT DOCUMENTS

| | | | |
|---|---|---|---|
| 2,499,045 A | | 2/1950 | Walker et al. |
| 3,455,298 A | | 7/1969 | Anstadt |
| 3,516,408 A | * | 6/1970 | Montanti |
| 3,667,069 A | * | 6/1972 | Blackshear et al. ......... 128/899 |
| 3,730,186 A | | 5/1973 | Edmunds, Jr. et al. |
| 3,791,374 A | | 2/1974 | Guarino |
| 3,995,623 A | | 12/1976 | Blake et al. |
| 4,309,994 A | * | 1/1982 | Grunwald |
| 4,345,602 A | * | 8/1982 | Yoshimura et al. ......... 604/275 |
| 4,407,271 A | | 10/1983 | Schiff |
| 4,423,725 A | | 1/1984 | Baran et al. |
| 4,459,977 A | | 7/1984 | Pizon et al. |
| 4,490,374 A | | 12/1984 | Bandurco et al. |
| 4,493,697 A | | 1/1985 | Krause et al. |
| 4,536,893 A | | 8/1985 | Parravicini |
| 4,546,759 A | | 10/1985 | Solar |

(List continued on next page.)

FOREIGN PATENT DOCUMENTS

| | | |
|---|---|---|
| DE | 43 24 637 A1 | 7/1993 |
| EP | 0 654 283 A1 | 11/1994 |
| EP | 0 884 064 A2 | 5/1998 |
| WO | WO 98/03213 | 1/1998 |
| WO | WO 98/17347 | 4/1998 |
| WO | WO 98/52639 | 11/1998 |
| WO | WO 99/33407 | 12/1998 |
| WO | WO 99/22784 | 5/1999 |
| WO | WO 99/51286 | 10/1999 |
| WO | WO 00/41612 | 1/2000 |

OTHER PUBLICATIONS

Katsumata et al., "Newly–Developed Catheter for Cardio–Renal Assist During Intraaortic Balloon Counterpulsation", *The Japanese Journal of Thoracic Surgery*, 1993, 46:767–770.

(List continued on next page.)

*Primary Examiner*—Brian L. Casler
*Assistant Examiner*—Jeremy Thissell
(74) *Attorney, Agent, or Firm*—John P. O'Banion; James C. Peacock, III

(57) ABSTRACT

Methods and apparatus are provided for treating congestive heart failure using a catheter having an inlet end configured for placement in the source of arterial blood such as the aorta, left ventricle or a femoral artery, and an outlet end having at least one conduit configured to be placed in the renal arteries. The catheter includes a lumen through which blood passes from the aorta or left ventricle directly to the renal artery, means for engaging the first conduit with renal artery. The means for engaging also may reduce backflow of blood into the abdominal aorta. The catheter preferably is configured to permit percutaneous, transluminal implantation. Methods of using and implanting the catheter are also provided.

1 Claim, 4 Drawing Sheets

U.S. PATENT DOCUMENTS

| | | |
|---|---|---|
| 4,554,284 A | 11/1985 | Stringer et al. |
| 4,685,446 A | 8/1987 | Choy |
| 4,705,502 A | 11/1987 | Patel |
| 4,705,507 A | 11/1987 | Boyles |
| 4,712,551 A * | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,817,586 A | 4/1989 | Wampler |
| 4,834,707 A | 5/1989 | Evans |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A * | 7/1990 | Jarvik ........................ 623/3.17 |
| 4,950,226 A * | 8/1990 | Barron .................. 604/101.01 |
| 4,957,477 A | 9/1990 | Lundback |
| 4,964,864 A | 10/1990 | Summers et al. |
| 4,976,691 A * | 12/1990 | Sahota ........................ 600/585 |
| 4,976,692 A | 12/1990 | Atad |
| 4,990,139 A | 2/1991 | Jang |
| 4,995,864 A * | 2/1991 | Bartholomew et al. ..... 604/153 |
| 5,002,532 A | 3/1991 | Gaiser et al. |
| 5,053,023 A | 10/1991 | Martin |
| 5,059,178 A | 10/1991 | Ya |
| 5,067,960 A | 11/1991 | Grandjean |
| 5,069,680 A | 12/1991 | Grandjean |
| 5,073,094 A * | 12/1991 | Dorman et al. ............. 417/412 |
| 5,089,019 A | 2/1992 | Grandjean |
| 5,098,370 A | 3/1992 | Rahat et al. |
| 5,098,442 A | 3/1992 | Grandjean |
| 5,112,301 A * | 5/1992 | Fenton et al. ................ 604/247 |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,163,910 A | 11/1992 | Schwartz et al. |
| 5,167,628 A | 12/1992 | Boyles |
| 5,180,364 A * | 1/1993 | Ginsburg .................... 600/435 |
| 5,205,810 A | 4/1993 | Guiraudon et al. |
| 5,226,888 A | 7/1993 | Arney |
| 5,256,141 A | 10/1993 | Gencheff et al. |
| 5,257,974 A | 11/1993 | Cox |
| 5,282,784 A | 2/1994 | Willard |
| 5,290,227 A | 3/1994 | Pasque |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,358,519 A | 10/1994 | Grandjean |
| 5,364,337 A | 11/1994 | Guiraudon et al. |
| 5,383,840 A | 1/1995 | Heilman et al. |
| 5,397,307 A | 3/1995 | Goodin |
| 5,429,584 A | 7/1995 | Chiu |
| 5,453,084 A * | 9/1995 | Moses |
| 5,464,449 A | 11/1995 | Ryan et al. |
| 5,484,385 A | 1/1996 | Rishton |
| 5,505,701 A | 4/1996 | Anaya Fernandez de Lomana |
| 5,509,428 A | 4/1996 | Dunlop |
| 5,558,617 A | 9/1996 | Heilman et al. |
| 5,609,628 A | 3/1997 | Keranen |
| 5,613,949 A * | 3/1997 | Miraki |
| 5,617,878 A | 4/1997 | Taheri |
| 5,643,171 A | 7/1997 | Bradshaw et al. |
| 5,643,215 A | 7/1997 | Fuhrman et al. |
| 5,702,343 A | 12/1997 | Alferness |
| 5,720,735 A * | 2/1998 | Dorros ........................ 604/284 |
| 5,755,779 A | 5/1998 | Horiguchi |
| 5,762,599 A | 6/1998 | Sohn |
| 5,776,190 A | 7/1998 | Jarvik |
| 5,797,876 A | 8/1998 | Spears et al. |
| 5,902,229 A | 5/1999 | Tsitlik et al. |
| 5,902,336 A | 5/1999 | Mishkin |
| 5,913,852 A * | 6/1999 | Magram ...................... 604/540 |
| 5,928,132 A | 7/1999 | Leschinsky |
| 5,935,924 A | 8/1999 | Bunting et al. |
| 5,971,910 A | 10/1999 | Tsitlik et al. |
| 5,984,955 A | 11/1999 | Wisselink |
| 6,077,256 A * | 6/2000 | Mann |
| 6,086,527 A | 7/2000 | Talpade |
| 6,117,117 A * | 9/2000 | Mauch |
| 6,165,120 A | 12/2000 | Schweich et al. |

OTHER PUBLICATIONS

Kehrer et al., "Construction and Experimental Application of a Catheter for Selective Arterial Kidney Perfusion in Situ", *Urological Research*, 1985, 13:85–89.

"FDA Form 510(K) on related correspondence for Advanced Equipment Development, Inc."

Fox, S. I.; "Mechanisms of Contraction," Human Physiology, Fourth Edition, pp. 300–323.

Cohn, Jay N.; "The Management of Chronic Heart Failure," The New England Journal of Medicine, pp. 490–498, Aug. 15, 1996.

Levin, Howard R. et al.; "Reversal of Chronic Ventricular Dilation in Patients with End–Stage Cardiomyopathy by Prolonged Mechanical Unloading," vol. 91, No. 11, pp. 2717–2718, Jun. 1, 1995.

Linden, R.J. et al.; "The Nature of the Atrial Receptors Responsible for a Reflex Decrease in Activity in Renal Nerves in the Dog," The Physiological Society, pp. 31–40, (1980).

Garwood, Susan et al.; "Renal Preservation Strategies for High Risk Patients," University of Chico School of Medicine, Cover Page, Table of Contents Page, pp. 1–19, (1998).

Postma, C.T. et al.; "Treatment of Renal Artery Stenosis with Intra–Arterial Stents," Ned Tijdschr Geneeskd, vol. 142, No. 39, pp. 2132–2137, Sep. 26, 1998. Abstract Only.

Jacobs, M.J. et al.; "Reduced Renal Failure Following Thoracoabdominal Aortic Aneurysm Repair by Selective Perfusion," Eur. J. Cardiothorac. Surg., vol. 14, No. 2, pp. 201–205, Aug., 1998. Abstract Only.

Novick, A.C.; "Atherosclerotic Ischemic Nephropathy. Epidemiology and Clinical Considerations," Urol. Clin. North Am., vol. 21, No. 2, pp. 195–200, May, 1994. Abstract Only.

Canaud, B. et al.; "Temporary Vascular Access for Extracorporeal Renal Replacement Therapies in Acute Renal Failure Patients," Kidney Int. Suppl., vol. 66, pp. S142–S150, May, 1998. Abstract Only.

White, C.J. et al., "Renal Artery stent Placement: Utility in Lesions Difficult to Treat with Balloon Angioplasty," J. Am. Coll. Cardiol., vol. 30, No. 6, pp. 1445–1450, Nov. 15, 1997. Abstract Only.

Iannone, L.A. et al.; "Effect of Primary Balloon Expandable Renal Artery Stents on Long–Term Patency, Renal Function, and Blood Pressure in Hypertensive and Renal Insufficient Patients with Renal Artery Stenosis," Cathet. Cardiovasc. Diagn., vol. 37, No. 3, pp. 243–250, Mar., 1996. Abstract Only.

Bergey, E.A. et al.; "Transhepatic Insertion of Vascular Dialysis Catheters in Children: A Safe, Life–Prolonging Procedure," Pediatr. Radiol., vol. 29, No. 1, pp. 42–50, Jan. 1999. Abstract Only.

Elkayam et al., Renal Vasodilatory Effect of Endothelial Stimulation in Patients with Chronic Congestive Heart Failure, J Am Coll Cardiol 1996;28: 176–182.

Masaki, Z. et al.; "In Situ Perfusion by Retrograde Cannulation of a Tumor Artery for Nephron–Sparing Surgery," Int. J. Urol, vol. 2, No. 3, pp. 161–165, Jul., 1995. Abstract Only.

Walker, H.S. et al.; "Use of a Balloon–Tipped Perfusion Catheter for Renal Preservation During Suprarenal Abdominal Aortic Operations," J. Vasc. Surg., vol. 2, No. 2, pp. 337–339, Mar., 1985. Abstract Only.

Seiter, H. et al.; "Modified T–Catheter and its Use for Transvenous Hypothermic in Situ Perfusion in the Surgical Restoration of the Kidney with Staghorn Calculi," Z. Urol Nephrol., vol. 76, No. 6 pp. 403–406, Jun., 1983. Abstact Only.

Eisenberger, F. et al.; "Transfemoral Cannulation of the Renal Vessels. Diagnostic and Therapeutic use in Urology," Urologe [A], vol. 16, No. 1, pp. 1–5, Jan., 1977. Abstract Only.

Bischoff, W. et al.; "Modified in Situ Perfusion of the Kidney Using Balloon Catheters," vol. 94, No. 30, pp. 1695–1697, Oct. 21, 1976. Abstract Only.

Kehrer, G. et al.; "Construction and Experimental Application of a Catheter for Selective Arterial Kidney Perfusion in Situ," Urol. Res., vol. 13, No. 2, pp. 85–89, (1985). Abstract Only.

Williams, D.M. et al.; "Design and Testing of a High–FLO2 Autoperfusion Catheter: An Experimental Study," J. Vasc. Interv. Radiol., vol. 3, No. 2, pp. 285–290, May, 1992. Abstract Only.

Kobayashi, A. et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682–684, May 25, 1992. Absract Only.

Greco, B.A. et al.; "Atherosclerotic Ischemic Renal Disease," Am. J. Kidney Dis., vol. 29, No. 2, pp. 167–187, Feb., 1997. Abstract Only.

Middleton, J.P.; "Ischemic Disease of the Kidney: How and Why to Consider Revascularization," J. Nephrol., vol. 11, No. 3, pp. 123–136, May–Jun., 1998. Abstract Only.

Katsumata, T. et al.; "Newly–Developed Catheter for Cardio–Renmal Assist During Intraaortic Balloon Counterpulsation," Kyobu Geka, vol. 46, No. 9, pp. 767–770, Aug., 1993. Abstract Only.

Akaba, N. et al.; "A Cylinder–Shaped Balloon Catheter for the Management of Dissecting Aneurysms in Acute Stage," Herz, vol. 17, No. 6, pp. 390–393, Dec., 1992. Abstract Only.

Mathis, J.M. et al.; "Use of a Guide Catheter as a Temporary Stent During, Microcatheter Intervention," AJNR Am. J. Neuroradiol, vol. 19 No. 5, pp. 932–933, May, 1998. Abstract Only.

\* cited by examiner

FIG. 2
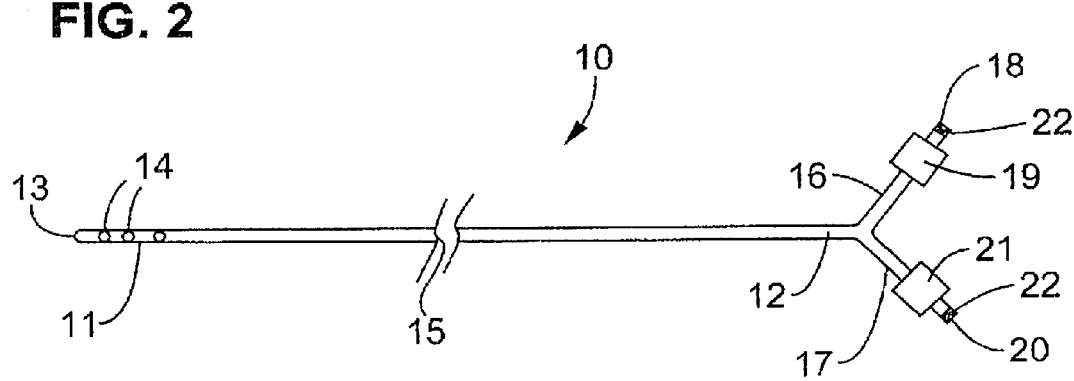
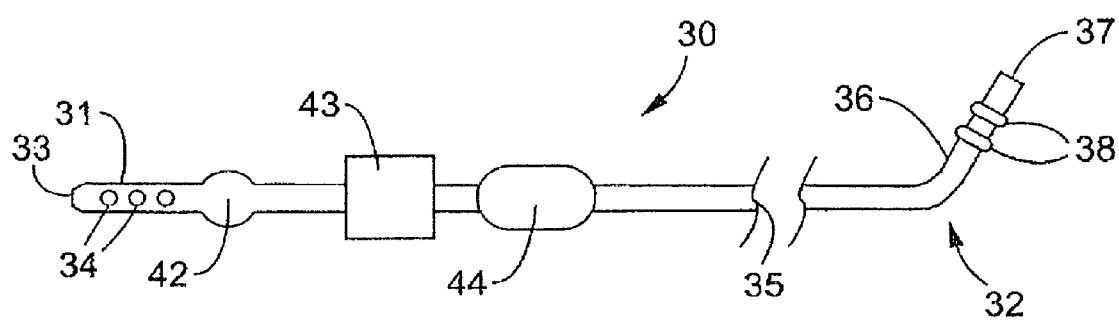
FIG. 3
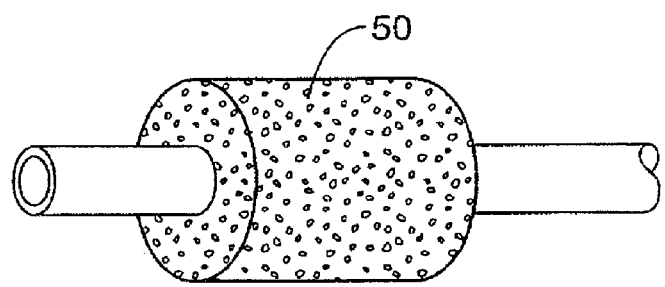
FIG. 4

APPARATUS AND METHODS FOR TREATING CONGESTIVE HEART DISEASE

FIELD OF THE INVENTION

The present invention relates to apparatus for treating congestive heart disease by providing increased perfusion to the kidneys, thereby enhancing renal function.

BACKGROUND OF THE INVENTION

It has long been known that cardiac dysfunction induces a series of events that ultimately contribute to congestive heart failure ("CHF"). One such event is a reduction in renal blood flow due to reduced cardiac output. This reduced flow can in turn result in the retention of excess fluid in the patient's body, leading for example, to pulmonary and cardiac edema.

Chapter 62 of *Heart Disease: A Textbook of Cardiovascular Medicine*, (E. Braunwald, ed., 5th ed. 1996), published by Saunders, Philadelphia, Pa., reports that for patients with CHF, the fall in effective renal blood flow is proportional to the reduction in cardiac output. Renal blood flow in normal patients in an age range of 20–80 years averages 600 to 660 ml/min/m$^2$, corresponding to about 14 to 20 percent of simultaneously measured cardiac output. Within a wide spectrum of CHF severity, renal blood flow is depressed to an average range of 250 to 450 ml/min/m$^2$.

Previously known methods of treating congestive heart failure and deteriorating renal function in patients having CHF principally involve administering drugs, including diuretics that enhance renal function, such as furosemide and thiazide, vasopressors intended to enhance renal blood flow, such as Dopamine, and vasodilators that reduce vasoconstriction of the renal vessels. Many of these drugs, when administered in systemic doses, have undesirable side-effects.

In addition, for patients with severe CHF (e.g., those awaiting heart transplant), mechanical methods, such as hemodialysis or left ventricular assist devices, may be implemented. Mechanical treatments, such as hemodialysis, however, generally have not been used for long-term management of CHF.

Advanced heart failure ("HF") requires the combination of potent diuretics and severe restriction of salt intake. Poor patient compliance is a major cause of refractoriness to treatment. On the other hand, as renal urine output decreases with reduced renal perfusion, in the event of dehydration, the required diuretic dosages increase.

In view of the foregoing, it would be desirable to provide methods and apparatus for treating and managing CHF without administering high doses of drugs or dehydrating the patient.

It further would be desirable to provide methods and apparatus for treating and managing CHF by improving blood flow to the kidneys, thereby enhancing renal function.

It also would be desirable to provide methods and apparatus for treating and managing CHF that permit the administration of low doses of drugs, in a localized manner, to improve renal function.

It still further would be desirable to provide methods and apparatus for treating and managing CHF using apparatus that may be percutaneously and transluminally implanted in the patient.

SUMMARY OF THE INVENTION

In view of the foregoing, it is an object of the present invention to provide methods and apparatus for treating and managing CHF without administering high doses of drugs or dehydrating the patient.

It is another object of this invention to provide methods and apparatus for treating and managing CHF by improving blood flow to the kidneys, thereby enhancing renal function.

It is also an object of this invention to provide methods and apparatus for treating and managing CHF that permit the administration of low doses of drugs, in a localized manner, to improve renal function.

It further is an object of the present invention to provide methods and apparatus for treating and managing CHF using apparatus that may be percutaneously and transluminally implanted in the patient.

These and other objects of the present invention are accomplished by providing a catheter having an inlet end configured for placement in a source of arterial blood, such as the aorta, the left ventricle or a femoral artery, and an outlet end having at least one conduit configured to be placed in a renal artery. The catheter includes a lumen through which arterial blood passes directly into a renal artery. The conduit may include means for engaging an interior surface of the renal artery to retain the conduit in position, and may comprise an occluder that reduces backflow of blood exiting the conduit into the abdominal aorta. The catheter preferably is configured to permit percutaneous, transluminal implantation.

In accordance with the principles of the present invention, high pressure blood passes through the lumen of the catheter during systole and into the conduit disposed in the renal artery. It is expected that blood passing through the catheter will have a higher pressure and higher flow rate than blood reaching the renal artery via the abdominal aorta. This in turn is expected to improve renal function, without administering systemic doses of drugs to improve renal function or renal blood flow. The enhanced renal blood flow is expected to provide a proportional increase in renal function, thereby reducing fluid retention.

In alternative embodiments, the catheter may include first and second conduits for perfusing both kidneys, a one-way valve disposed in the lumen to prevent backflow of blood in the lumen during diastole or a mechanical pump to further enhance the flow of blood through the lumen. Still other embodiments of the catheter may include a drug infusion reservoir that injects a low dose of a drug, e.g., a diuretic or vasodilator, into blood flowing through the lumen, so that the drug-infused blood passes directly into the kidneys. Still further embodiments may comprise separate catheters to perfuse the left and right kidneys, or may draw arterial blood from a peripheral vessel using an external pump.

Methods of implanting the apparatus of the present invention also are provided.

BRIEF DESCRIPTION OF THE DRAWING

Further features of the invention, its nature and various advantages will be more apparent from the accompanying drawings and the following detailed description of the preferred embodiments, in which:

FIG. 2 is a side view of an illustrative embodiment of the apparatus of the present invention;

FIG. 3 is an alternative embodiment of the apparatus of FIG. 2 including a one-way valve, a blood pump and a drug infusion device;

FIG. 4 is a detailed perspective view of an occluder employed on the outlet end of the catheter of FIG. 2.

DETAILED DESCRIPTION OF THE INVENTION

The present invention provides a catheter that may be implanted in patients suffering from congestive heart failure ("CHF") to improve renal blood flow and renal function. In accordance with the principles of the present invention, it is expected that by passing blood from the left ventricle directly to the renal arteries during systole, the blood pressure and flow rate in the kidneys will be increased, resulting in enhanced renal function.

Figure 1:
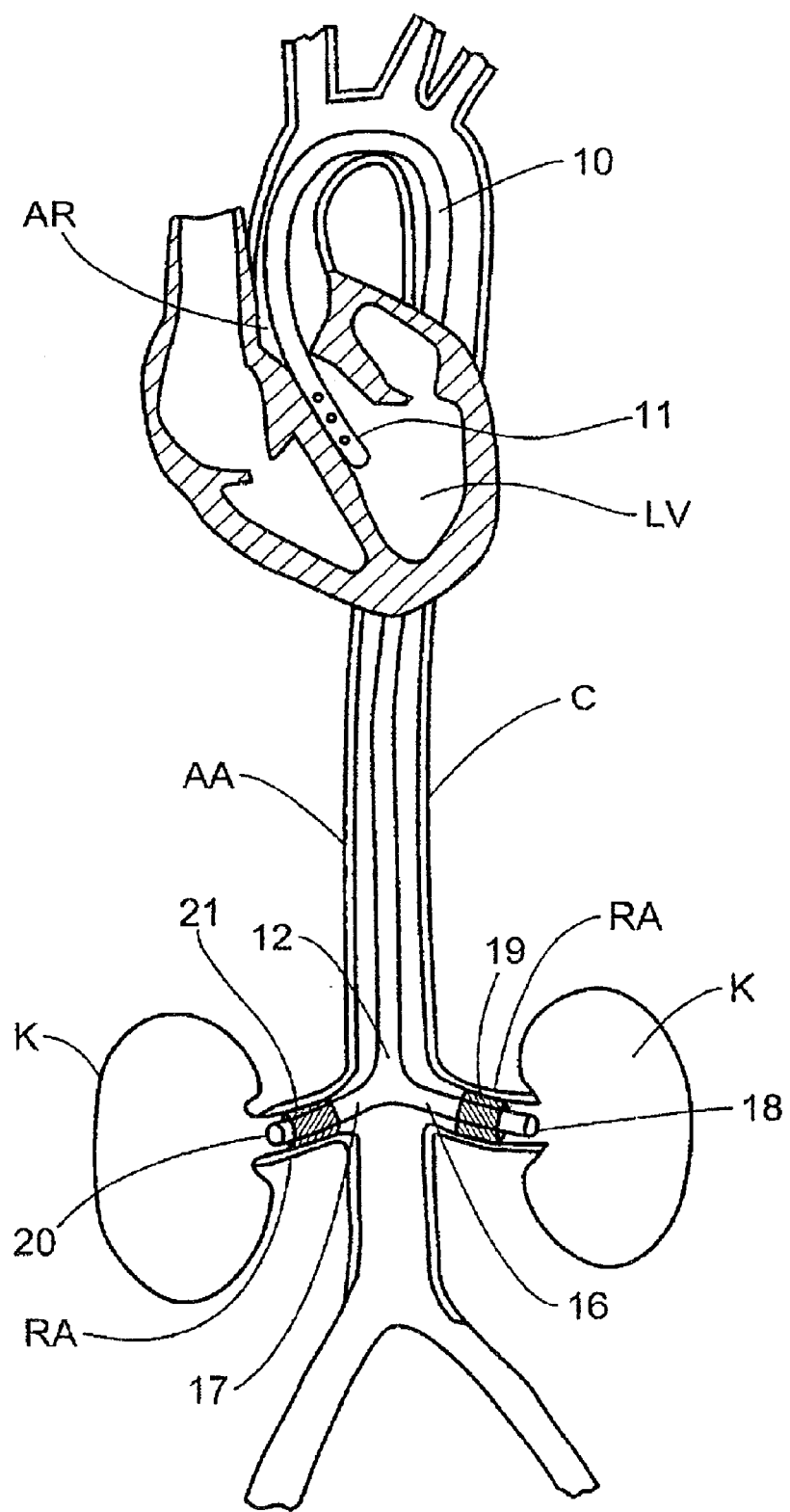
FIG. 1 is a partial sectional view of a human circulatory system having apparatus constructed in accordance with the present invention implanted therein.

Referring to FIGS. 1 and 2, a first illustrative embodiment of apparatus constructed in accordance with the principles of the present invention is described. Catheter 10 comprises hollow flexible tube having inlet end 11 and outlet end 12. Inlet end 11 includes distal hole 13 and lateral holes 14 that communicate with lumen 15 within catheter 10. Outlet end 12 comprises first and second branch conduits 16 and 17, respectively. Catheter 10 preferably comprises a flexible biocompatible material, such as polyurethane, silicone, or polyethylene.

First branch conduit 16 includes outlet port 18 that communicates with lumen 15, and expandable occluder 19. Likewise, second branch conduit 17 includes outlet port 20 that communicates with lumen 15, and expandable occluder 21. First and second branch conduits 16 and 17 optionally may include radio-opaque marker bands 22 near outlet ports 18 and 20, respectively, to assist in implanting catheter 10.

As depicted in FIG. 1, catheter 10 is implanted in circulatory system C so that inlet end 11 is disposed in left ventricle LV or in the vicinity of aortic root AR, while first and second branch conduits 16 and 17, respectively, are disposed in renal arteries RA. Occluders 19 and 21, described in greater detail hereinafter, engage the walls of the renal arteries and retain first and second branch conduits 16 and 17, respectively in position. The occluders also serve to prevent backflow of high pressure blood exiting through outlet ports 18 and 20 from flowing backwards into abdominal aorta AA. Accordingly, blood entering catheter 10 via distal hole 13 and lateral holes 14 during systole passes directly into renal arteries RA and kidneys K through lumen 15, thereby enhancing renal blood flow and renal function.

Referring now to FIG. 3, an alternative embodiment of the apparatus of the present invention is described. Catheter 30 is similar in construction to catheter 10 of FIG. 1, and includes hollow flexible tube having inlet end 31 and outlet end 32. Inlet end 31 includes distal hole 33 and lateral holes 34 that communicate with lumen 35. Outlet end 32 comprises branch conduit 36 having outlet port 37 configured to be placed in one of the patient's renal arteries. In this embodiment, the occluder of the embodiment of FIG. 2 is omitted and instead the diameter of the branch conduit 36 is selected to provide a close fit with the renal artery. Engagement means, such as small ribs or barbs 38 also may be disposed on the exterior surface of branch conduit 36 to retain the branch conduit in the renal artery.

Because the renal arteries may branch from the abdominal aorta at different levels, the catheter of FIG. 3 advantageously permits separate catheters to be used to each perfuse only a single kidney. In addition, the inlet end of catheter 30 may be configured to be placed in a peripheral vessel rather than the left ventricle.

Catheter 30 further optionally comprises any one or more of the following components: one-way valve 42, blood pump 43 or drug infusion device 44. While catheter 30 illustratively includes all three of the foregoing components, it is to be understood that any combination of such components advantageously may be employed.

One-way valve 42, if provided, is configured to open during systole to permit blood to flow through lumen 35 from left ventricle LV towards the renal artery RA, but closes during diastole to prevent the left ventricle from drawing blood in the opposite direction.

Blood pump 43, if provided, may comprise an implantable blood pump, such as are known in the art, and serves to enhance renal blood flow in those patients suffering from severe cardiac dysfunction. Alternatively, where the inlet end of catheter 30 is configured to be placed in a peripheral vessel, blood pump 30 advantageously may comprise an external blood pump, such as are known in the art.

Drug infusion device 44, if provided, preferably comprises an implantable infusion device, such as are known in the art (e.g., for chelation therapy), and periodically infuses low doses of therapeutic agents into blood flowing through lumen 35. Because the infused drugs are delivered directly into the kidneys, smaller doses may be employed, while achieving enhanced therapeutic action and fewer side-effects.

With respect to FIG. 4, an illustrative embodiment of occluder 50 suitable for use with the catheter of FIGS. 1 and 2 is described. In one embodiment, occluder 50 comprises a low density, biocompatible sponge-like material that may be compressed to a small thickness, and that absorbs and expands when exposed to body fluid. In particular, occluder 50 preferably is compressed to a small thickness and then mounted on the branch conduit so that, when the occluder is deployed in a renal artery, it swells and engages the interior of the renal artery.

Occluder 50 therefore serves to retain the branch conduit in position in a renal artery, and also reduces backflow of blood from the renal artery into the abdominal aorta. Alternatively, occluder 50 may comprise an inflatable member that is inflated and then sealed via a lumen (not shown) extending out of the patient's femoral artery. As a yet further alternative, occluder 50 may comprise a self-expanding hydrogel material that swells when exposed to body fluids to accomplish the functions described hereinabove.

While occluder 50 of FIG. 4 illustratively has an annular shape, it should be understood that other shapes may be employed. For example, occluder 50 may be configured to only partially surround the branch conduit, and may provide only a partial seal with the interior surface of the renal artery. For example, depending upon the relative sizes of the branch conduit and the renal artery, and how far the branch conduit extends into the renal artery, occluder 50 may be omitted altogether.

Figure 5A:
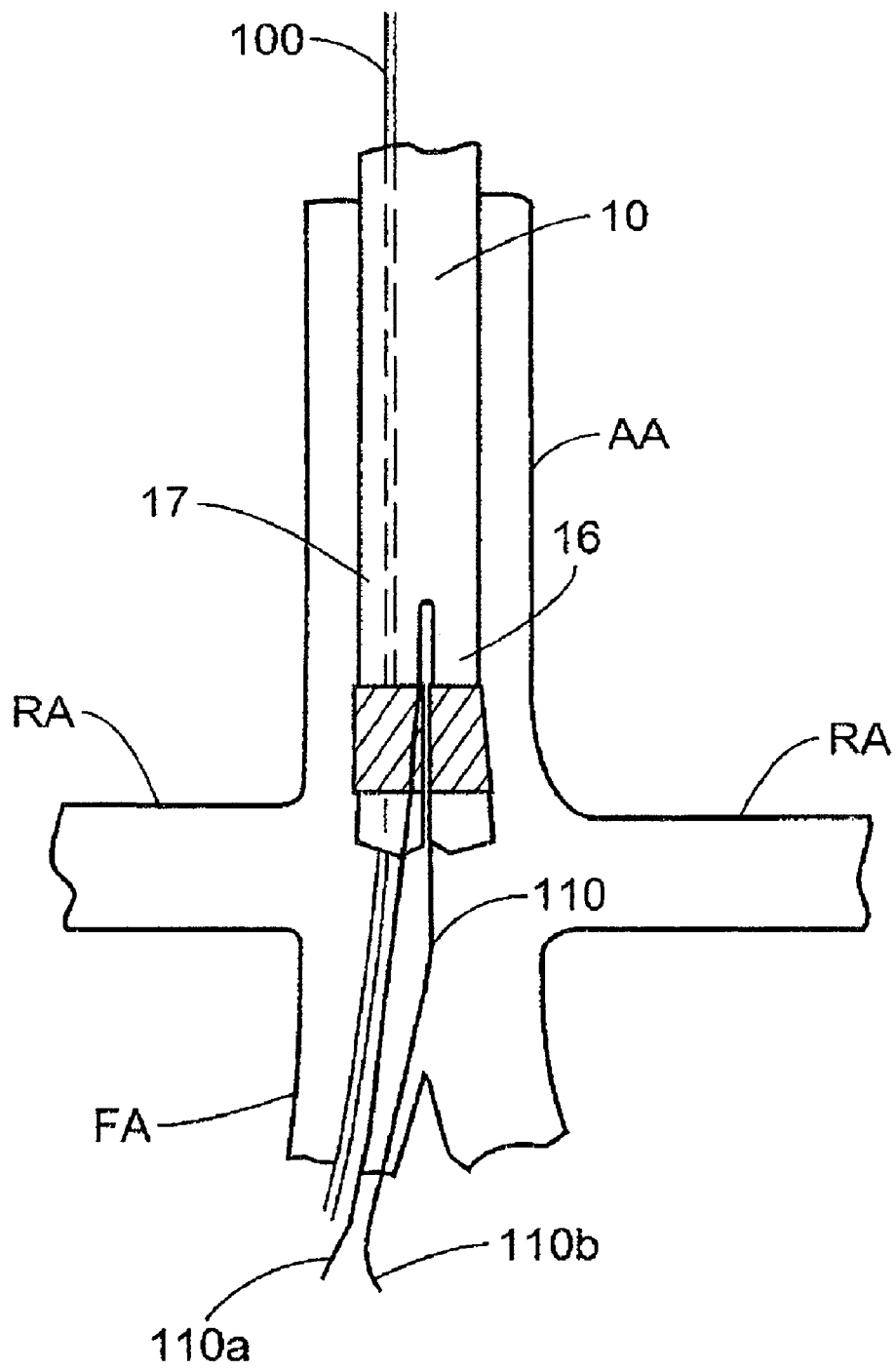
FIGS. 5A and 5B are partial sectional views depicting an illustrative method of implanting the catheter of FIG. 2.
Figure 5B:
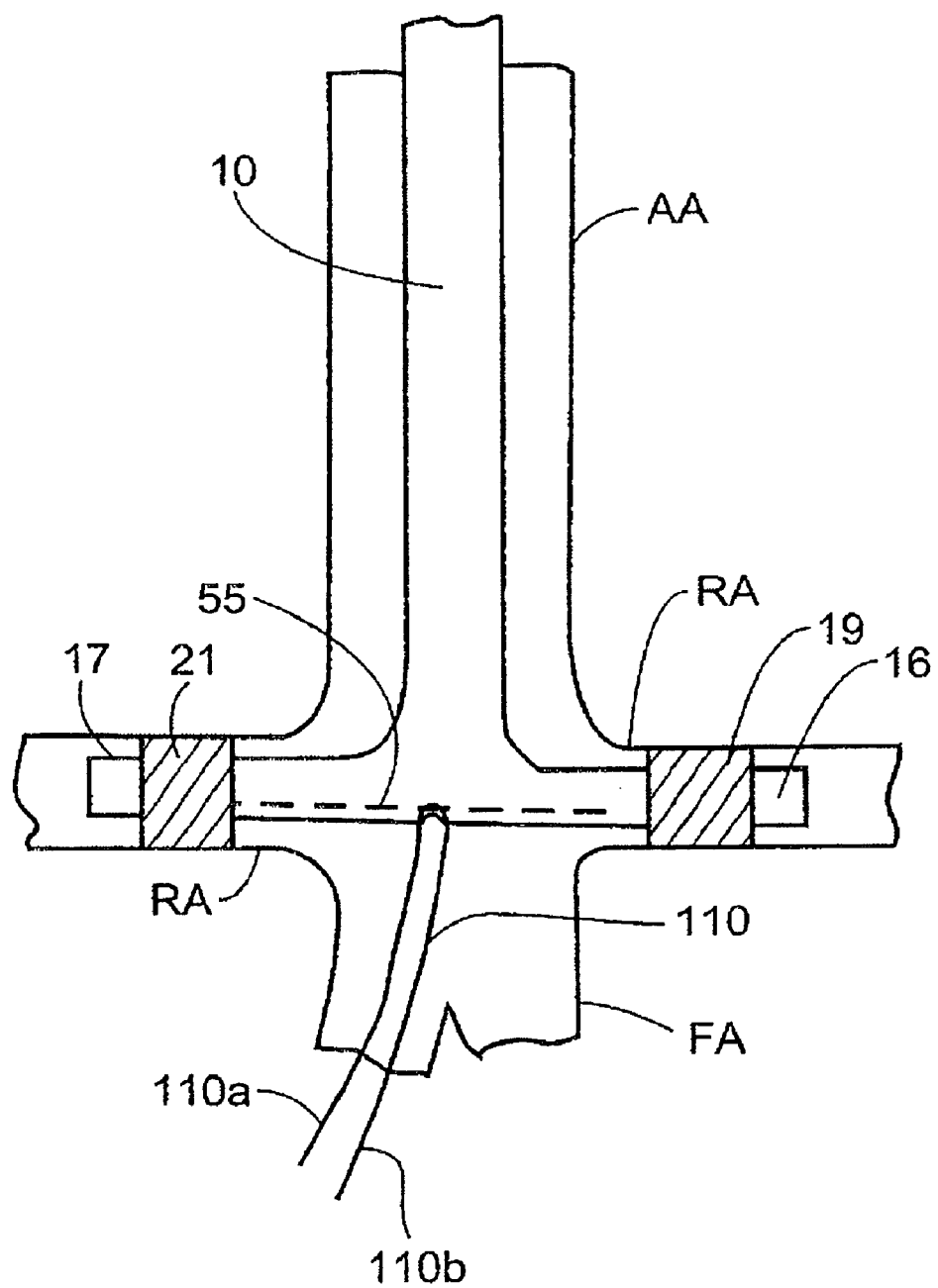

Referring now to FIGS. 1, 5A and 5B, percutaneous, transluminal implantation of the apparatus of FIG. 2 is described. First, guidewire 100 is inserted in a retrograde manner through abdominal aorta AA via an access site in femoral artery FA until the tip of the guidewire is disposed in the left ventricle, e.g., as determined by fluoroscopy. Catheter 10 is then advanced along guidewire 100, for example, using a push tube (not shown) disposed on guidewire 100, with first and second branch conduits 16 and 17 folded side-by-side. Filament 110 is looped through a small opening at the bifurcation of the first and second branch conduits 16 and 17, so that the free ends 110a and 110b of loop 110 may be manipulated by the surgeon.

As depicted in FIG. 5A, catheter 10 is pushed in a distal direction so that outlet ports 18 and 20 of outlet end 12 clear the renal arteries, and guidewire 100 is withdrawn. Filament 110 then is pulled in the proximal direction so that the ends of the first and second branch conduits move into renal arteries RA, as illustrated in FIG. 5B. Strand 55 of an elastic, high strength material, such as a nickel-titanium alloy, may be embedded in the wall of catheter 10 in the bifurcation to ensure that the first and second conduits open outwardly when catheter 10 is pulled in a proximal direction by filament 110.

Once the position of first and second branch conduits 16 and 17 is confirmed, for example, by observing the location of radio-opaque markers 22 (see FIG. 2) with a fluoroscope, occluders 19 and 21 expand to engage the interior surfaces of the renal arteries. Expansion of the occluders may be accomplished either by holding the occluders in place while they expand (if self-expanding) or, if the occluders are inflatable, by injecting a suitable inflation medium.

Filament 110 then may be pulled completely through the opening in the bifurcation of catheter 10, leaving catheter 10 implanted in position. It is expected that the opening needed to accommodate filament 110 will result in negligible loss of blood through the opening once filament 110 has been withdrawn. Alternatively, or in addition, additional guidewires (not shown) may be disposed through first and second branch conduits to assist in placing the first and second branch conduits in renal arteries RA.

The foregoing methods may be readily adapted to implant two catheters of the type illustrated in FIG. 3, so that the branch conduit of each catheter perfuses a separate kidney. In addition, for acute treatment of CHF, the catheter of FIG. 3 (including an external blood pump) may be placed so that the inlet end is disposed in a patient's femoral artery, and the outlet end is disposed in one of the patient's renal arteries.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. A method of locally perfusing one or more kidneys comprising:

providing a flexible catheter having an inlet region with an inlet port, an outlet region comprising a conduit with an outlet port, and a lumen extending between the inlet port and the outlet port;

providing a blood pump;

advancing the catheter percutaneously and transluminally along a guidewire to dispose the inlet port in a source of arterial blood;

inserting the conduit into a patient's renal artery while maintaining blood flow through the aorta and past the renal artery;

engaging the conduit within the patient's renal artery by at least partially occluding the renal artery, where by blood flows through said lumen along the conduit and through the outlet port directly into the renal artery; and actuating the blood pump to increase a rate of blood flow through the lumen.

* * * * *